United States Patent
David

(10) Patent No.: US 9,585,737 B2
(45) Date of Patent: *Mar. 7, 2017

(54) DENTAL FLOSS DEVICE

(71) Applicant: Yair David, Ramat Hasharon (IL)

(72) Inventor: Yair David, Ramat Hasharon (IL)

( * ) Notice: Subject to any disclaimer, the term of this patent is extended or adjusted under 35 U.S.C. 154(b) by 121 days.

This patent is subject to a terminal disclaimer.

(21) Appl. No.: 14/045,078

(22) Filed: Oct. 3, 2013

(65) Prior Publication Data

US 2014/0026922 A1 Jan. 30, 2014

Related U.S. Application Data

(63) Continuation-in-part of application No. 13/405,364, filed on Feb. 27, 2012, now abandoned, which is a continuation-in-part of application No. 12/901,536, filed on Oct. 10, 2010, now Pat. No. 8,127,778.

(51) Int. Cl.
*A61C 15/04* (2006.01)
*A61C 15/00* (2006.01)

(52) U.S. Cl.
CPC ............ *A61C 15/043* (2013.01); *A61C 15/04* (2013.01)

(58) Field of Classification Search
CPC ......... A61C 15/00; A61C 15/02; A61C 15/04; A61C 15/043; A61C 15/046
USPC ....... 132/323, 324, 329, 311, 309, 314, 327; 206/225, 226, 83, 368, 388, 63.3, 63.5, 206/822, 227, 49; 606/224, 225, 227
See application file for complete search history.

(56) References Cited

U.S. PATENT DOCUMENTS

| | | | | |
|---|---|---|---|---|
| 753,543 A | * | 3/1904 | Case | B65D 59/04 |
| | | | | 206/226 |
| 3,212,502 A | * | 10/1965 | Myers | A61B 17/06 |
| | | | | 24/706 |
| 3,831,611 A | | 8/1974 | Hendricks | |
| 4,040,433 A | | 8/1977 | Edison | |
| 4,403,625 A | * | 9/1983 | Sanders | A61C 15/046 |
| | | | | 132/323 |
| 4,519,408 A | * | 5/1985 | Charatan | A61C 15/043 |
| | | | | 132/321 |

(Continued)

FOREIGN PATENT DOCUMENTS

| CN | 201734796 | | 2/2011 |
|---|---|---|---|
| GB | 2289845 | A | 12/1995 |

(Continued)

OTHER PUBLICATIONS

U.S. Appl. No. 09/747,127, filed Oct. 18, 2001, Berhman C. Mark et al.

(Continued)

*Primary Examiner* — Tatiana Nobrega
(74) *Attorney, Agent, or Firm* — Pearl Cohen Zedek Latzer Baratz LLP

(57) ABSTRACT

A method and a dental floss device for flossing the teeth of a user, and a production process of the dental floss device, in accordance with an embodiment of the present invention. The dental floss device includes a single use dental floss packaged inside a dental tubule. The dental tubule does not practically limit the bending capability of the dental floss wherein the dental floss device is adapted to be inserted into a ball, having a ball internal volume and for takes up at least 70 percent of the ball internal volume.

25 Claims, 8 Drawing Sheets

(56) References Cited

U.S. PATENT DOCUMENTS

| | | | |
|---|---|---|---|
| 4,828,108 A * | 5/1989 | Roth | A61C 19/06 206/368 |
| 4,832,063 A * | 5/1989 | Smole | A61C 15/041 132/321 |
| 4,852,728 A | 8/1989 | Court | |
| 4,886,049 A * | 12/1989 | Darras | A61B 1/00142 600/124 |
| 4,986,289 A | 1/1991 | McWhorter | |
| 5,050,625 A * | 9/1991 | Siekmann | A61C 15/045 132/323 |
| 5,102,332 A * | 4/1992 | Uthoff | A61O 5/007 206/63.5 |
| 5,174,314 A | 12/1992 | Charatan | |
| 5,322,077 A | 6/1994 | Corella | |
| 5,406,965 A | 4/1995 | Levine | |
| 5,454,386 A | 10/1995 | Dix | |
| 5,503,168 A | 4/1996 | Wang | |
| 5,549,201 A | 8/1996 | Braude | |
| 5,566,692 A | 10/1996 | Thornton | |
| 5,582,194 A | 12/1996 | Dolan | |
| 5,692,610 A * | 12/1997 | Porteous | A61C 9/0033 206/368 |
| 5,735,299 A | 4/1998 | Kaltenbach | |
| 5,794,776 A | 8/1998 | Corella | |
| 5,819,767 A * | 10/1998 | Dix | A61C 15/043 132/321 |
| 5,890,500 A * | 4/1999 | Mabon | A61C 15/041 132/321 |
| 5,913,418 A | 6/1999 | Singh | |
| 5,915,392 A | 6/1999 | Isaac | |
| 6,102,051 A | 8/2000 | Neves | |
| 6,220,257 B1 | 4/2001 | Meyer et al. | |
| 6,234,182 B1 * | 5/2001 | Berglund | A61C 15/046 132/323 |
| 7,665,600 B1 | 2/2010 | Griffin | |
| 2004/0065342 A1 | 4/2004 | Sharman | |
| 2004/0168703 A1 | 9/2004 | Cho | |
| 2005/0006263 A1 * | 1/2005 | Tsaur | B65D 85/24 206/368 |
| 2005/0115854 A1 | 6/2005 | Miles | |
| 2007/0131242 A1 | 6/2007 | Fleck | |
| 2007/0277845 A1 | 12/2007 | Blasco | |
| 2010/0139688 A1 | 6/2010 | Musgrave | |
| 2012/0279518 A1 * | 11/2012 | Alas | A61C 15/046 132/324 |
| 2013/0276814 A1 * | 10/2013 | Alas | A61C 15/046 132/309 |

FOREIGN PATENT DOCUMENTS

| WO | WO 03/045271 A1 | 6/2003 |
|---|---|---|
| WO | PCT/JP02/11289 | 10/2003 |

OTHER PUBLICATIONS

U.S. Appl. No. 10/265,528, filed Apr. 8, 2004, Sherman Thomas
U.S. Appl. No. 11/170,858, filed Jan. 12, 2006, Brajnovic Izidor
U.S. Appl. No. 12/239,168, filed Jan. 15, 2009, Lyulyev Vyacheslav et al.
U.S. Appl. No. 11/221,542, filed Mar. 8, 2007, Stelmach Thomas.

* cited by examiner

DENTAL FLOSS DEVICE

REFERENCE TO CROSS-RELATED APPLICATION

This application claims priority from and is a Continuation-in-Part of U.S. patent application Ser. No. 13/405,364 filed on Feb. 27, 2012, which claims priority from and is a Continuation-in-Part of U.S. patent application Ser. No. 12/901,536 filed on Oct. 10, 2010, now U.S. Pat. No. 8,127,778.

FIELD OF THE INVENTION

The present invention relates to oral hygiene, more particularly, to single use dental floss, and more particularly, to a dental floss device including dental floss packed within a tubule.

BACKGROUND OF THE INVENTION

To maintain dental hygiene, it is important to clean the teeth every so often, and to remove food remnants from between the teeth. At present, various means are used for this purpose, dental floss being one of the most efficient means currently available. One particularly popular means is lengths of waxed dental floss, contained within a dispenser, wound onto a spool, with one end protruding slightly. In preparation for use, the user pulls the end of the dental floss, exposing the desired length of floss from the dispenser, and then cuts it and uses it.

The length of the dental floss contained within the dispenser can be, for example, 50 meters. A typical length of the length cut for the purpose of use can be approximately 30 centimeters, although the American Dental Association recommends flossing at least once a day, using a dental floss having a length of about 46 centimeters.

There are many situations in which a user knows that there will be a need for a single-use package of dental floss, such as for example, when going out to a restaurant and continuing straight on from there to another event. In this case, carrying a dispenser with an unnecessary length of dental floss, and continued carrying of the dispenser are inconvenient.

In order to meet the need for small and convenient means of dental flossing, several solutions have been proposed, such as a fork-like with two prongs and a short length of dental floss stretched between them. However, those who prefer a more thorough cleaning with the dental floss wound on their own fingers, one from each hand, do not find such solution satisfactory.

Packages of short pieces of dental floss for single use have been proposed. An oral hygiene device, which is disposable single use package, is described in U.S. Pat. No. 4,852,728 of Court.

FIG. 1 of the prior art illustrates the disposable single use package 60 of Court. The single use package 60 includes a dental floss 10 at a length suitable for single use, a first triangularly shaped leaf 61 and a second triangularly shaped leaf 62. The first triangularly shaped leaf 61 and the second triangularly shaped leaf 62 are connected to each other by means of a common ridge. When in storage, they are folded onto each other, and prior to use, they are opened, to enable removal of the dental floss 10.

A single use dental floss dispenser is described in U.S. Pat. No. 5,582,194 of Dolan.

FIG. 2 of the prior art illustrates the single use dental floss dispenser 70 of Dolan.

The single use dental floss dispenser 70 of Dolan includes a dental floss 10 at a length suitable for single use, disposed within a cover portion 71, which is closed for storage by means of a lid portion 72. The lid portion 72 is opened prior to use, to enable removal of the dental floss 10.

As used herein dental floss 10 is waxed or un-waxed thin filament or thread designed to be used for cleaning the teeth and the spaces between them.

Dental floss 10 can be made as a single filament or comprising many fibers from different materials, such as silk, Nylon (polyamide), Polytetrafluoroethylene (PTFE), a well known brand name of PTFE is Teflon by DuPont Co., polyethylene, and polypropylene or mixtures of two or more thereof, and can also contain flavors and other ingredient materials.

Dental floss can have several different cross-sections shapes and dimensions.

In spite of all of the known and existent solutions, there is still a need for a short length of dental floss, conveniently packaged for single use. It is possible to simply pre-cut a short length of dental floss and store it in one's pocket, until it is removed from the pocket for use. This would be the most convenient solution in terms of storage, volume, and weight; however, in this manner the dental floss cannot be kept sufficiently clean, and can cause infections in the user's mouth.

There is a need for a device including a short length of dental floss, for single use, whose size, volume, weight, and pliability are similar to those of bare dental floss, which maintaining sanitary conditions during carrying in the user's pocket. Such a device would be suitable for use at restaurants and other places and events, such as at businesses and venues, similarly to the toothpicks provided in suitable dispenser on the table or countertop.

SUMMARY OF THE INVENTION

The background art does not teach or suggest a short length of single use dental floss, which is contained in a protective package prior to use, the package adding only minimal necessary weight, volume, and bending restrictions, thus enabling convenient carrying, with the contained dental floss, in one's pocket, and enabling easy and convenient extraction of the dental floss from the package.

According to the teachings of the present invention, there is provided a dental floss device including: (a) a dental tubule having a dental tubule first end, a dental tubule second end, a dental tubule length, and a dental tubule inner surface; and (b) a dental floss having a dental floss first end, a dental floss second end, a dental floss length approximately equal the length of the dental tubule, and a dental floss outer surface, wherein at least most of the dental floss is contained within the dental tubule, wherein the dental floss device is adapted to be inserted into a ball having a ball internal volume and for taking up at least 70 percent of the ball internal volume, and wherein the dental floss device is adapted to enable extracting of the dental floss fully from the dental tubule.

According to another feature of an embodiment of the present invention, the dental floss device has an overlapping zone wherein, in the overlapping zone, there is full contact between the dental floss outer surface and the dental tubule inner surface, wherein the dental tubule is substantially pressing on the dental floss along the entire of the overlapping zone.

According to another feature of an embodiment of the present invention, the dental floss device has a dental floss device length of at most 50 centimeters, wherein the dental floss device is adapted to enable being scraped to a shape that is suitable to be closed by the ball while the dental floss captures most of the ball internal volume, by applying a pressing force of at most 3 Newton.

According to another feature of an embodiment of the present invention, the dental floss has an exposed segment which extends longitudinally beyond the second end of the dental tubule, wherein the dental floss device has a dental floss device volume, wherein the dental floss device is adapted to be inserted into a ball having a ball internal volume, and wherein the ball internal volume equals at most 1.45 times of the dental floss device volume.

According to another feature of an embodiment of the present invention, the dental tubule has an empty segment, wherein the empty segment includes no dental floss.

According to the teaching of the present invention, there is provided a dental floss device including: (a) a dental tubule having a dental tubule first end, a dental tubule second end a dental tubule length, and a dental tubule inner surface; and (b) a dental floss having a dental floss first end, a dental floss second end, a dental floss length approximately equal the length of the dental tubule, and a dental floss outer surface, wherein at least most of the dental floss is contained within the dental tubule, wherein the dental floss device is adapted to be provided with a shape of a planar spiral having a spiral outer diameter, wherein the spiral outer diameter is at most equal to 0.06 times of the dental floss length, and wherein the dental floss device is adapted to enable extracting of the dental floss fully from the dental tubule.

According to another feature of an embodiment of the present invention, the dental floss device has an overlapping zone, wherein, in the overlapping zone, there is full contact between the dental floss outer surface and the dental tubule inner surface, wherein the dental tubule is substantially pressing on the dental floss along the entirety of the overlapping zone.

According to another feature of an embodiment of the present invention, the dental floss has a spiral outer diameter, wherein the spiral outer diameter is at most equal to 0.06 times of the dental floss length, and the dental floss has an exposed segment which extends longitudinally beyond the second end of the dental tubule.

According to another feature of an embodiment of the present invention, the dental tubule of the dental floss device has a spiral outer diameter and an empty segment, wherein the spiral outer diameter is at most equal to 0.06 times the dental floss length, and the empty segment includes no dental floss.

According to the teaching of the present invention, there is provided a dental floss device including: (a) a dental tubule having a dental tubule first end, a dental tubule second end, a dental tubule cross-sectional area value, a dental tubule length, and a dental tubule inner surface; and (b) a dental floss having a dental floss first end, a dental floss second end, a dental floss length, a dental floss cross-sectional area value, and a dental floss outer surface, wherein at least most of the dental floss is contained within the dental tubule, wherein the dental floss device has an overlapping zone, wherein the dental tubule cross-sectional area value is equal at most to a pre-determined n-times the dental floss cross-sectional area value, wherein the n-value is selected from a group consisting of one, two and three, and wherein the dental floss device is adapted to enable extracting of the dental floss fully from the dental tubule.

According to another feature of an embodiment of the present invention, in the overlapping zone. there is full contact between the dental floss outer surface and the dental tubule inner surface, wherein the dental tubule is substantially pressing on the dental floss along the entire of the overlapping zone, and the dental floss length approximately equal the length of the dental tubule.

According to another feature of an embodiment of the present invention, the dental floss has bending characteristics, wherein the dental tubule has a dental tubule wall having a suitable dental tubule wall thickness, regarding the bending characteristics of the dental tubule, wherein the dental tubule is made of a suitable material, regarding the bending characteristics of the dental tubule, wherein the dental tubule does not create any substantial bending restriction on a segment of the dental floss contained within the dental tubule at the overlapping zone.

According to another feature of an embodiment of the present invention, the dental floss of the dental floss device has a dental tubule cross-sectional area value that equals at most a pre-determined n times the dental floss cross-sectional area value, and the dental floss has an exposed segment which extends longitudinally beyond the second end of the dental tubule.

According to another feature of an embodiment of the present invention, the dental tubule of the dental floss device has a dental tubule cross-sectional area value that is equal at most a pre-determined n-times of the dental floss cross-sectional area value, and the dental tubule has an empty segment, wherein the empty segment includes no dental floss.

According to another feature of an embodiment of the present invention, the dental floss of the dental floss device has a dental tubule cross-sectional area value that is equal to, at most, a pre-determined n-times the dental floss cross-sectional area value, and the dental floss has an exposed segment which extend longitudinally beyond the second end of the dental tubule.

According to another feature of an embodiment of the present invention, the dental tubule of the dental floss device has a dental tubule cross-sectional area value that is equal to, at most a pre-determined n-times the dental floss cross-ssectional area value, and the dental tubule has an empty segment, wherein the empty segment includes no dental floss.

According to another feature of an embodiment of the present invention, the dental tubule has a dental tubule interior volume, wherein the dental floss has a dental floss volume, and wherein the dental tubule interior volume is approximately equal the dental floss volume.

According to another feature of an embodiment of the present invention, the dental tubule has an empty segment having an empty segment length, wherein the dental floss has an exposed segment having an exposed segment length, and wherein the empty segment length is approximately equal the exposed segment length.

According to another feature of an embodiment of the present invention, the dental tubule has a dental tubule weight, wherein there is a segment near the dental floss second end having a segment near the dental floss second end length, wherein the segment near the dental floss second end length is at most ten percent of the overlapping zone, wherein there is a pressure acting on the dental floss at the segment near the dental floss second end, wherein the pressure is stronger than any other pressure applied by the dental tubule on the dental floss at any segment other than the segment near the dental floss second end, and wherein a pulling force needed for extraction the dental floss from the dental tubule is at most equal to the dental tubule weight.

According to another feature of an embodiment of the present invention, the dental floss device further includes: (c) a pressing ring mounted on the dental tubule at the segment near the dental floss second end.

Additional objects and advantages of the invention will be set forth in part in the description which follows and, in part, will be obvious from the description, or may be learned by practice of the invention.

BRIEF DESCRIPTION OF THE DRAWINGS

The invention is herein described, by way of example only, with reference to the accompanying drawings, wherein.

Figure 1:
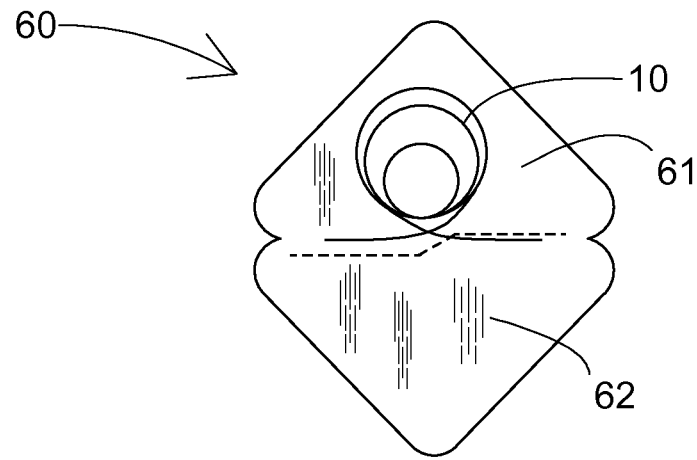
FIG. 1 of the prior art illustrates a disposable use package.
Figure 2:
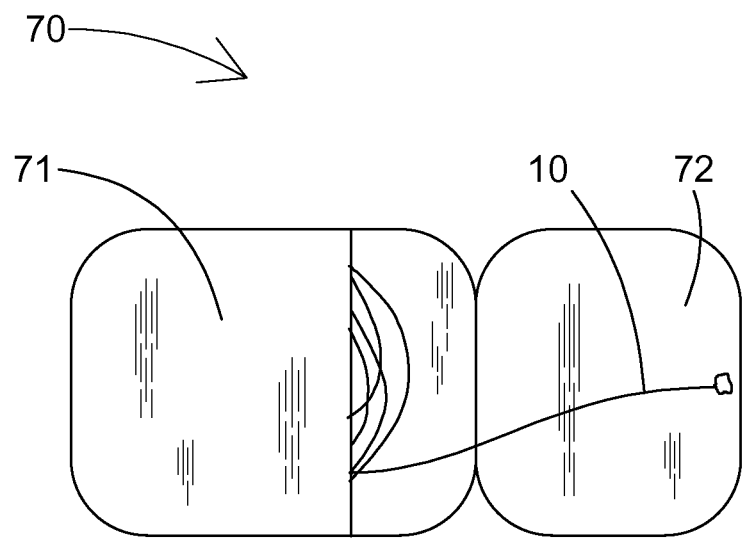
FIG. 2 of the prior art illustrates a single use dental floss dispenser.

In order to leave no room for doubt, the elements shown in the illustrations of the present patent application in a manner that enables understanding them clearly, and the scales, size relations, and shapes are not in any way limiting their embodiment.

DETAILED DESCRIPTION OF EMBODIMENTS OF THE INVENTION

To remove any doubt, note that the manner in which the elements of the present invention are described in the illustrations can be highly detailed; however, the manner in which the elements of the present invention are described in the illustrations does not in any way limit the present invention, and is for the purpose of clarification and furthering understanding. The present invention can be implemented in embodiments that differ from the specification given with regard to the illustration.

The present invention is of a dental floss device. The principles and operation of a dental floss device according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

As used herein the specification and in the claims section that follows, the term 'single use' refer to use of dental floss for cleaning in one session between the teeth of a user.

This definition is to distinguish this use from that of a long length of dental floss, from which dental floss is occasionally cut at the desired length for cleaning between the teeth, with the long length of dental floss being able to be cut many times, until there is not enough dental floss left for use.

As used herein the specification and in the claims section that follows, the term 'dental tubule' refers to a tubule having suitable qualities for use as a component of a dental floss device, according to the present invention.

The following list is a legend of the numbering of the application illustrations:

10 dental floss
10a dental floss first end
10b dental floss second end
10c dental floss core
10d coating layer
10l dental floss length
10od dental floss outer diameter
10os dental floss outer surface
10t dental floss cross-sectional thickness
10v dental floss volume 10w dental floss cross-sectional width
10A dental floss cross-sectional area
10W dental floss weight
11 exposed segment
11*l* exposed segment length
20 dental tubule
20*a* dental tubule first end
20*b* dental tubule second end
20*id* dental tubule interior diameter
20*is* dental tubule inner surface
20*l* dental tubule length
20*od* dental tubule outer diameter
20*t* dental tubule wall thicknesses
20*iv* dental tubule interior volume
20*v* dental tubule volume
20*w* dental tubule wall
20A dental tubule cross-sectional area
20W dental tubule weight
21 empty segment
21*l* empty segment length
22 segment near the empty segment
22*l* segment near the empty segment length
25 cap
27 overlapping zone
29 bending radius
31 local gap
35 pressing ring
40*l* left hand
40*r* right hand
41 finger
50 threading device
51 hook
60 disposable single use package (prior art, according to Court)
61 first triangularly shaped leaf (prior art, according to Court)
62 second triangularly shaped leaf (prior art, according to Court)
70 dental floss dispenser (prior art, according to Dolan)
71 cover portion (prior art, according to Dolan)
72 lid portion (prior art, according to Dolan)
80 card
82 adhesive layer
85 spiral outer diameter
87 spiral pitch
90 ball
91 ball wall
92 ball wall thickness
93 ball internal diameter
94 ball internal volume
100 dental floss device
100*l* dental floss device length
100*v* dental floss device volume
$F_1$ pressing force
$F_2$ pulling force
P pressure Hereinafter, embodiments of the present invention are explained in detail by referring to the drawings.

Figure 3A:
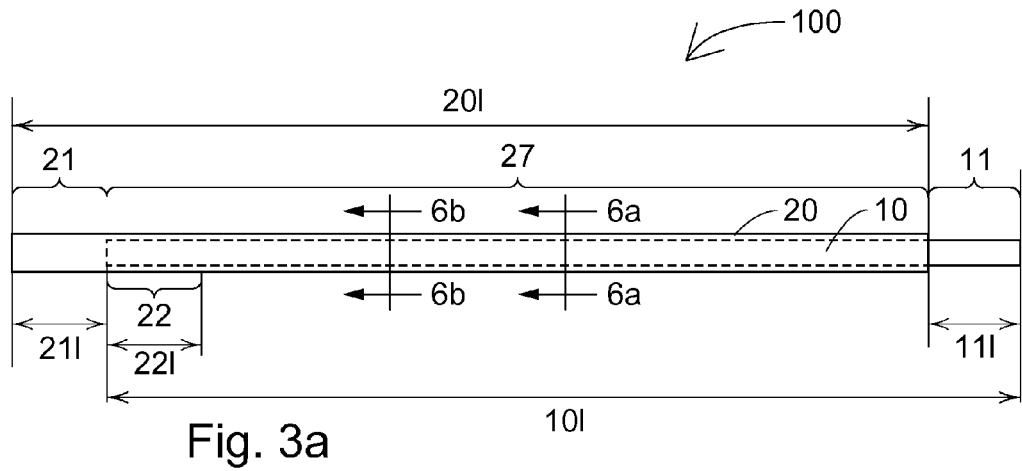
FIG. 3a is a side view schematic illustration of a dental floss device, in accordance with an embodiment of the present invention, upon which section planes 6a-6a and 6b-6b are marked.

FIG. 3*a* is a side view schematic illustration of a dental floss device 100, in accordance with an embodiment of the present invention, upon which section planes 6*a*-6*a* and 6*b*-6*b* are marked.

The present illustration shows a state of storage and carrying of the dental floss device 100, however for the purpose of clarity, it is shown straight, without any folds.

A dental floss 10 having a dental floss length 10*l* is mostly disposed within a dental tubule 20.

For example, for a dental floss 10 having a dental floss length 10*l* of about 46 centimeters, about 44 centimeters of the dental floss 10 are disposed within a dental tubule 20.

The dental tubule 20 has a dental tubule length 20*l* is open at one end and can be closed at the other end, to prevent infiltration of contaminants.

According to the present invention, the dental tubule length 20*l* can be, approximately equal to the dental floss length 10*l*.

The dental floss 10 has an exposed segment 11, having an exposed segment length 11*l* which serves the purpose of enabling the fingers of one hand of the user to grasp it, when pulling from the dental tubule 20, and the dental tubule 20 has a empty segment 21 having an empty segment length 21*l*, which serves the purpose of enabling the fingers of the other hand of the user to grasp it when pulling.

According to the present invention, the exposed segment length 11*l* can be, equal approximately to the empty segment length 21*l*.

A segment near the empty segment 22, having a segment near the empty segment length 22*l* exist near the empty segment 21.

The segment of the dental tubule 20 containing the dental floss 10 is referred to as an overlapping zone 27. The overlapping zone 27 is at is largest during the production process or during storage, and become smaller when pulling dental floss 10, and does not exist at all when the pulling is completed and the dental floss 10 is fully extracted.

For the purpose of clarity of details, the present illustration, as well as some of the following illustrations, shows the dental floss 10 and the dental tubule 20 with exaggeratedly large diameters in proportion to their lengths, relative to their actual proportion.

Using here the term diameter does not necessarily means that the dental floss 10 has a cross-sectional shape of a circle. The two section planes 6*a*-6*a* and 6*b*-6*b* are marked here upon one dental floss device 100 for illustration of two different cross-sectional shapes of two different dental flosses 10, just in order to save one drawing.

The dental tubule 20 is designated to maintain the hygiene of the segment of the dental floss 10 that intended to clean between the teeth, contained within. Important features of the dental tubule 20 are imperviousness to contaminants and, as far as possible, not to create any bending restrictions, which do not apply to the dental floss 10 itself, while being strong enough to be resistant to tearing. A moderate bending restriction such as enabling a dental floss device 100 radius bending, not larger then, for example, 5 millimeters is also in the scope of the present invention.

The structural material of the dental tubule 20 and its dimensions should be selected accordingly.

A good selection of the dental tubule 20 material is that of the same structural material of the specific dental floss 10, of the dental floss device 100, or at least of one of its components. It is desirable to select material that does not cause allergic reactions, such as structural material customarily used for medical tubules.

Suitable materials are, among others, Polytetrafluoroethylene (PTFE). A well known brand name of PTFE is Teflon by DuPont Co., Polypropylene, Polyurethane, Polyisoprene, Latex, Silicon, Polyethylene, such as low density Polyethylene (LDPE), such as from 0.91 up to 0.94 grams per one cubic centimeter, known as Nylon, or high density Polyethylene (HDPE), such as from 0.94 up to 0.97 grams per one cubic centimeter.

However, these materials are in no way limiting the present invention.

The dental floss device 100 is configured to enable extraction of the dental floss 10 fully from the dental tubule 20, using moderate manual force. For this purpose it is desired to use a waxed dental floss 10 as a component of the dental floss device 100.

Figure 3B:
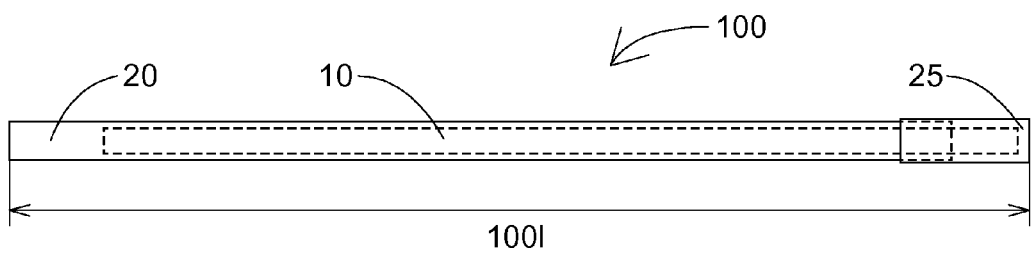
FIG. 3b is a side view schematic illustration of a dental floss device, including a cap, in accordance with an embodiment of the present invention.

FIG. 3b is a side view schematic illustration of a dental floss device 100, including a cap 25, in accordance with an embodiment of the present invention.

The cap 25 improves the sterility of dental floss 10.

The dental floss device 100 has an overall dental floss device length 100l, that includes the cap 25.

Figure 4:
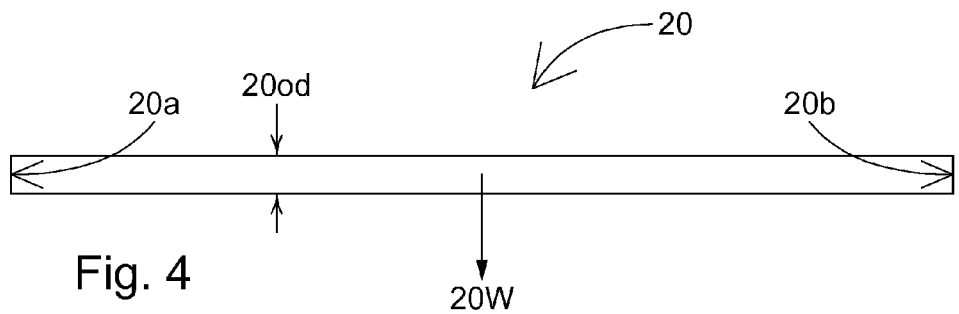
FIG. 4 is a side view schematic illustration of a dental tubule of the dental floss device, in accordance with an embodiment of the present invention.

FIG. 4 is a side view schematic illustration of a dental tubule 20 of the dental floss device 100, in accordance with an embodiment of the present invention.

Dental tubule 20 has a dental tubule first end 20a, a dental tubule second end 20b, a dental tubule outer diameter 20od, in case of circular shape cross-section, and inherently a dental tubule weight 20W.

Figure 5:
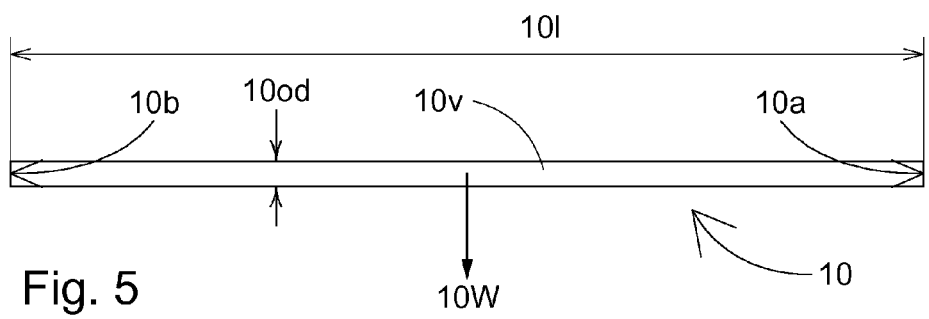
FIG. 5 is a side view schematic illustration of a dental floss of the dental floss device, in accordance with an embodiment of the present invention.

FIG. 5 is a side view schematic illustration of a dental floss 10 of the dental floss device 100, in accordance with an embodiment of the present invention.

The dental floss 10 has a dental floss first end 10a, a dental floss second end 10b, a dental floss outer diameter 10od, in case of circular shape cross-section, an inherent dental floss weight 10W, and a dental floss volume 10v, which is the dental floss cross-sectional area 10A (not shown in the present drawing), multiplied by the dental floss length 10l.

Figure 6A:
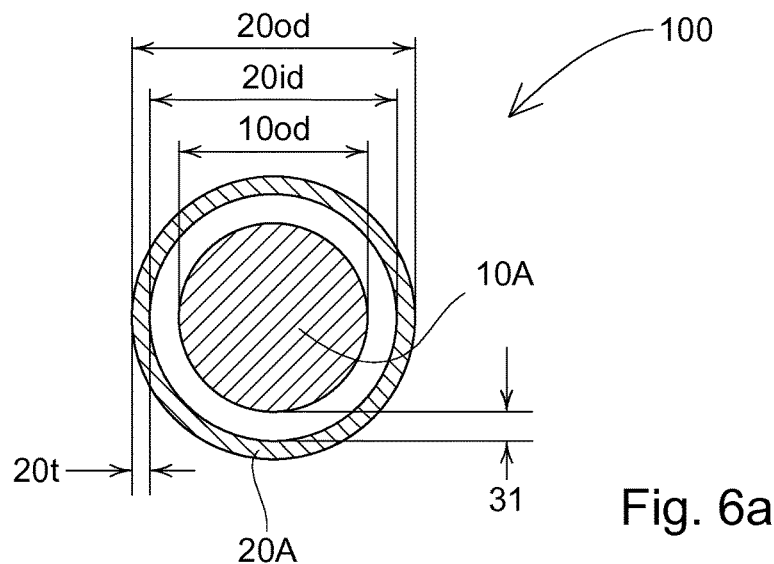
FIG. 6a is a cross sectional view 6a-6a of a dental floss device having a circular cross section, in accordance with an embodiment of the present invention.

FIG. 6a is a cross sectional view 6a-6a of a dental floss device 100 having a circular cross section, in accordance with an embodiment of the present invention.

The dental tubule 20 has a dental tubule interior diameter 20id.

A local gap 31, the value of which can vary in different location along the cross section, and along the overlapping zone 27 (not shown in the present illustration, shown in FIG. 3a), can exist between the dental floss 10 and the dental tubule 20.

In an embodiment, of the present invention, there is no local gap 31 other than along the entire overlapping zone 27.

In another embodiment of the present invention, the local gap 31 must equal zero, only along the segment near the empty segment 22 (not shown in the present illustration, shown in FIG. 3a), which is a short segment of the overlapping zone 27, such as one or two centimeters or even one or two millimeters. In such a case, like that at the very beginning of the extraction of the dental floss 10 from the dental tubule 20 there is a need to use a pulling force $F_2$ (not shown in the present illustration, shown in FIG. 8b), in order to overcome the friction force acting on that short segment, and after that a reduced force is sufficient.

The dental tubule wall thickness 20t, which is the dental tubule outer diameter 10od minus the dental tubule interior diameter 20id divided by two, is an important factor regarding the bending characteristic of the dental tubule 20.

The dental floss cross-sectional area 10A equal approximately $\pi \times$(the dental floss outer diameter 10od/2)$^2$ and the dental tubule cross-sectional area 20A equals approximately $\pi \times$(the dental tubule interior diameter 20id)$\times$(the dental tubule wall thickness 20t).

Figure 6B:
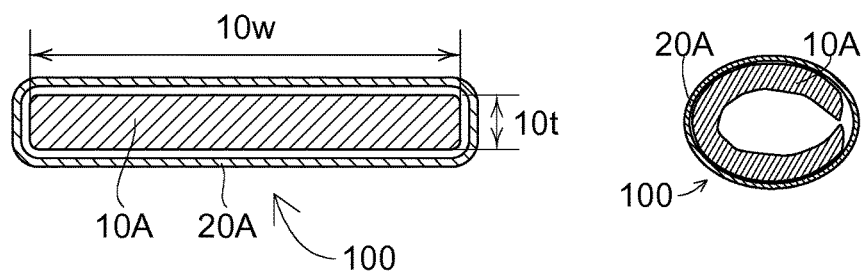
FIG. 6b is a cross sectional view 6b-6b of a dental floss device having a dental floss having a rectangular cross section, in accordance with an embodiment of the present invention.
Figure 6C:
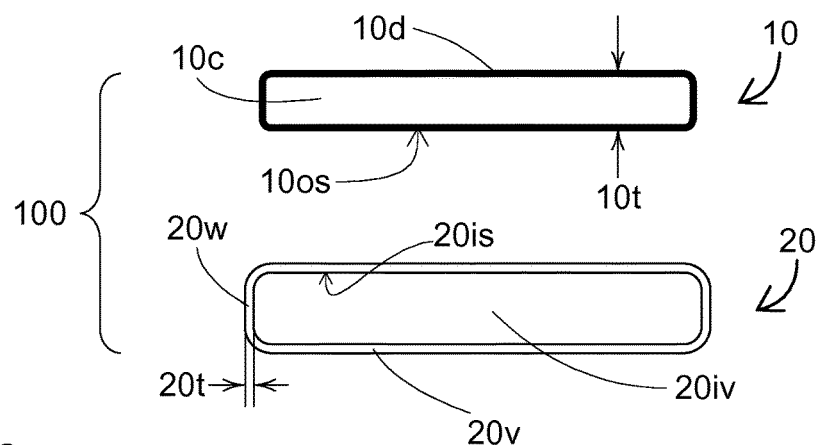
FIG. 6c is a front view exploded schematic illustration of a dental floss device having a rectangular cross section, in accordance with an embodiment of the present invention.

The dental tubule cross-sectional area 20A does not includes the cross-sectional area of the dental tubule interior volume 20iv (shown on FIG. 6c).

One of the most important properties of the present invention is that the dental tubule 20 does not create any substantial bending restriction on the dental floss bending characteristics. In order to achieve this property, the dental tubule 20 needs to have a dental tubule cross-sectional area 20A small enough in relation to the dental floss cross-sectional area 10A. Practically, it is sufficient for materials such as Teflon, Nylon and others, that the dental tubule cross-sectional area 20A be not greater than the dental floss cross-sectional area 10A, in other words has a dental tubule wall thickness 20t smaller than a quarter of the dental floss outer diameter 10od.

It is possible, according to the present invention, to enable the use of dental tubule 20 that slightly limits the dental floss 10 bending capability, or capabilities, in case that the dental floss 10 has different bending capabilities at different directions. For example a dental floss device 100 bending radius of five millimeters, can be acceptable. Therefore, it is within the scope of the present invention, to produce a dental floss device 100 having a dental tubule cross-sectional area 20A n-times larger than the dental floss cross-sectional area 10A; with n having, for example, any one of the values 2, 3, 4, or 5. The user can choose a dental floss device 100 having an n-value according to preference from the dental floss devices 100 on the shelf, accordingly with the corresponding bending characteristics.

This description is not limited to a specific dental floss cross-sectional shape.

FIG. 6b is a cross sectional view 6b-6b of a dental floss device 100 having a dental floss 10 having a rectangular cross section, in accordance with an embodiment of the present invention.

The present invention is not limited in any way to dental floss 10 having any specific floss cross-sectional shape and dimensions. In any place in the present document, in the description and in the claims section wherein reference is made to a dental floss 10, of the dental floss device 100, the intention is to the specific dental floss 10 that was selected to be combined with a dental tubule 20 for constituting a dental floss device 100, according to the present invention.

On the left side of the present drawing, a rectangular shape shows a dental floss cross-section width 10w, a dental floss cross-sectional thickness 10t, a dental floss cross-section area 10A, and a dental tubule cross-section area 20A.

When the ratio of the dental floss cross-section width 10w to the dental floss cross-sectional thickness 10t is large enough and the pressing power activated by the dental tubule 20 on the dental floss 10 is also large enough, it is possible that the cross-section shape of the dental floss 10 will be distorted, and will fold, for example, as shown at the right side of the current drawing. In such a case it is clear that that full contact between the dental floss 10 and the dental tubule 20 will not exist.

Typically, in the market, the dental floss cross-sectionals 10A are up to approximately 0.25 square millimeters.

FIG. 6c is a front view exploded schematic illustration of a dental floss device 100 having a rectangular cross section, in accordance with an embodiment of the present invention.

The dental floss 10 illustrated in the present drawing has a dental floss core 10c and a coating layer 10d, a dental floss cross-sectional thickness 10t, and a dental floss outer surface 10os, which is the most outer surface of the dental floss 10, including the coating layer 10d.

If the dental floss 10 has no coating layer 10d, the dental floss outer surface 10os is the outer surface of the dental floss core 10c.

The dental floss cross-sectional thickness 10t is measured from the dental floss outer surfaces 10os of two opposite sides.

The dental tubule 20 has a dental tubule wall 20w having a dental tubule wall thickness 20t, and a dental tubule inner surface 20is.

The dental tubule 20 has a dental tubule interior volume 20*iv* which is the volume enclosed inside the dental tubule inner surface 20*is* along the entire dental tubule length 20*l* (not shown in the present drawing).

The dental tubule 20 has a dental tubule volume 20*v* which is the volume of the material composing the dental tubule 20, namely, practically, the product of the dental tubule cross-section area 20A (shown in FIG. 6*b*) multiplied by the dental tubule length 20*l* (shown in FIG. 3*a*).

As used herein the specification and in the claims section that follows, the dental floss device volume 100*v* is the sum of the dental tubule volume 20*v* and the dental floss volume 10*v*.

According to an embodiment of the present invention, as long as there is at least a segment of the dental floss 10 inside the dental tubule 20, there is practically full contact between the dental floss outer surfaces 10*os* of that segment to the dental tubule inner surface 20*is* along the length of the overlapping zone 27 (not shown in the present drawing, shown in FIG. 3*a*).

Figure 7A:
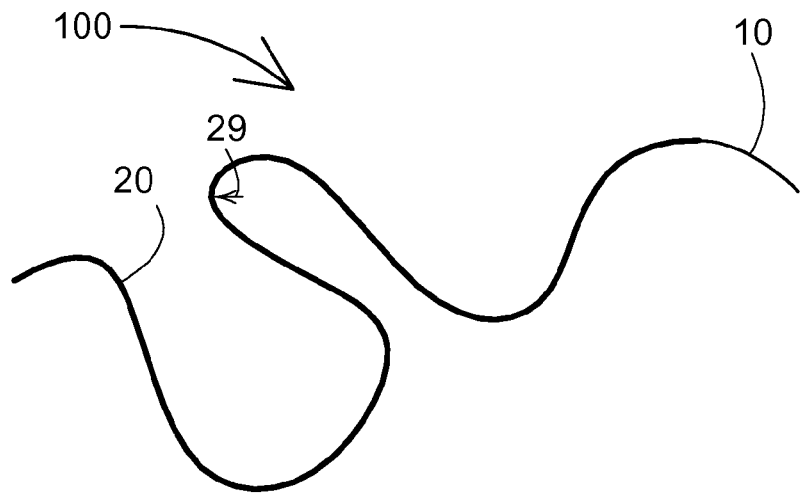
FIG. 7a is a top view schematic illustration of a dental floss device, in accordance with an embodiment of the present invention.

FIG. 7*a* is a top view schematic illustration of a dental floss device 100, in accordance with an embodiment of the present invention.

The illustration demonstrates the torsion of the dental floss device 100.

A bending radius 29, no larger than 5 millimeters, is sufficient for all practical purposes of carrying the dental floss device 100.

Figure 7B:
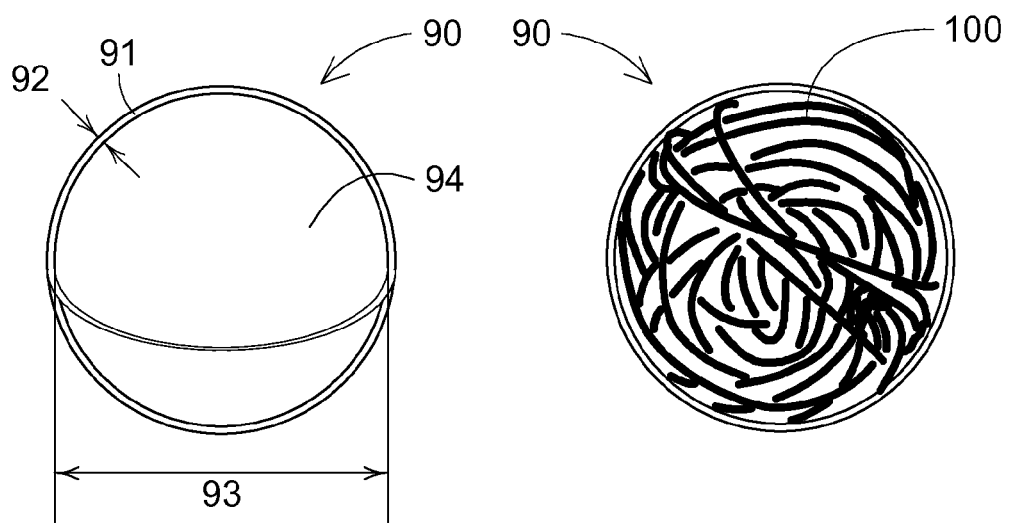
FIG. 7b is an isometric view schematic illustration of two balls, one of which is loaded with a dental floss device, in accordance with an embodiment of the present invention.

FIG. 7*b* is an isometric view schematic illustration of two balls 90, one of which is loaded with a dental floss device 100, in accordance with an embodiment of the present invention.

The two balls 90 are illustrated as having transparent walls 91. The right ball 90 contains a dental floss device 100, folded with many times.

The dental floss device 100 can be folded neatly and take a form, for example, of a skein of wool, or be folded at random.

Ball 90 has a ball wall 91, a ball wall thickness 92, a ball internal diameter 93, and a ball internal volume 94, and can be made, for example, of two parts, as shown at the left side of the present drawing.

A dental floss device 100, as in the present invention, having a dental tubule 20 which does not create substantial restriction on the dental floss 10 bending capability, can be inserted into a ball 90 in a way that will fulfill the most of the ball internal volume 94, for example, 70 percent of it.

Namely the ball internal volume 94 equals at most approximately 1.45 times of the dental floss device volume 100*v* (not shown in the present drawing).

For example, according to the present invention, a dental floss length 10*l* (shown in FIG. 3*a*) of 40 centimeters, having a dental floss cross-sectional area 10A (shown in FIGS. 6*a* and 6*b*) of 0.25 square millimeters is sufficient for practical purposes to provide the dental floss device 100 as configured to be inserted into a ball 90 having a ball internal diameter 93 of less than 2 centimeters.

Figure 8A:
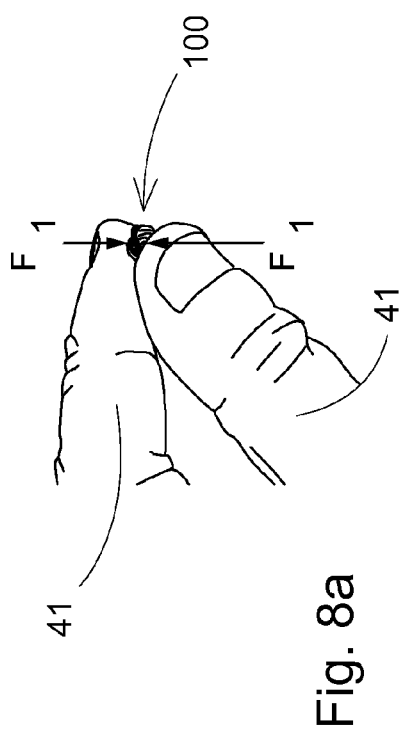
FIG. 8a is an isometric view schematic illustration of two fingers applying a pressing force on a dental floss device, in accordance with an embodiment of the present invention.

FIG. 8*a* is an isometric view schematic illustration of two fingers 41 applying pressing forces $F_1$ on a dental floss device 100, in accordance with an embodiment of the present invention.

A dental floss device 100, according to the present invention, can take the form of a skein, as was described regarding FIG. 7*b*, by being wound between two fingers 41. A moderated pressing force $F_1$, such as of 3 Newton is sufficient to obtain a dental floss device 100 that can be inserted into a ball 90 (not shown in the present illustration), in such a way that it will make the most efficient use of the ball internal volume 94 (not shown in the present illustration), for example, 70 percent of the ball internal volume 94, as was described regarding FIG. 7*b*.

When the user suffices with a dental floss device 100 that makes use of a smaller percentage of the ball internal volume 94 by applying the same pressing force $F_1$ of 3 Newton, it is possible to alter the features of dental tubule 20 (not shown in the present illustration) structure, such as the material type, the value of the dental tubule cross-sectional area 20A (not shown in the present illustration), and the value of the dental tubule wall thickness 20*t* (not shown in the present illustration).

Figure 8B:
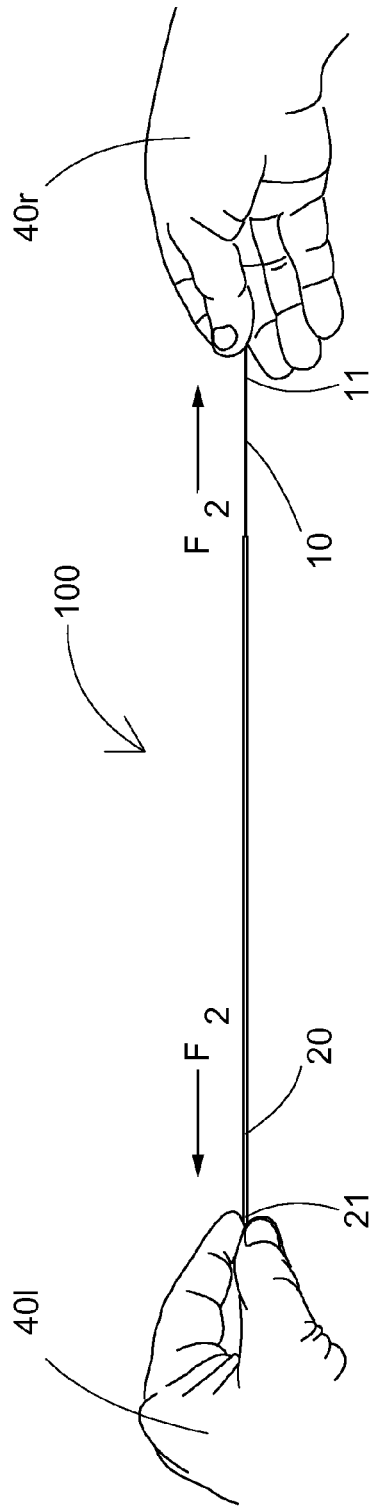
FIG. 8b is an isometric view schematic illustration of two hands performing an operating stage of the dental floss device, in accordance with an embodiment of the present invention.

FIG. 8*b* is an isometric view schematic illustration of two hands, 40*l* and 40*r*, performing an operating stage of the dental floss device 100, in accordance with an embodiment of the present invention.

This stage can be started from an initial state in which the dental floss device 100 has an arbitrary shape also including the shapes shown in FIGS. 7*a*, 7*b*, 8*a*, 12*a*, and 12*b*.

In the case shown in the present illustration, the left hand 40*l* grips the empty segment 21, the right hand 40*r* grips the exposed segment 11, and each one pulls with pulling force $F_2$ for the purpose of removal. The force required for removal grows smaller as the removal progresses. The necessary pulling force $F_2$ is determined also by the friction coefficient, the pressure P (shown in FIG. 10*a*), if existent, applied by the dental tubule 20 on the dental floss 10 and the length of the overlapping zone 27 (shown in FIG. 3*a*).

The necessary pulling force $F_2$ must not be too small, in order to prevent accidental removal, but must also not be so large as to pose difficulty during removal and to risk tearing the dental tubule 20 during removal. Therefore, the design and production of the dental floss device 100 are performed so that the necessary pulling force $F_2$ will be in the range between two predetermined values.

A reasonable minimal value of the pulling force $F_2$, under which removal will not occur, which is the larger of twice the dental tubule weight 20W and twice the dental floss weight 10W.

Figure 9:
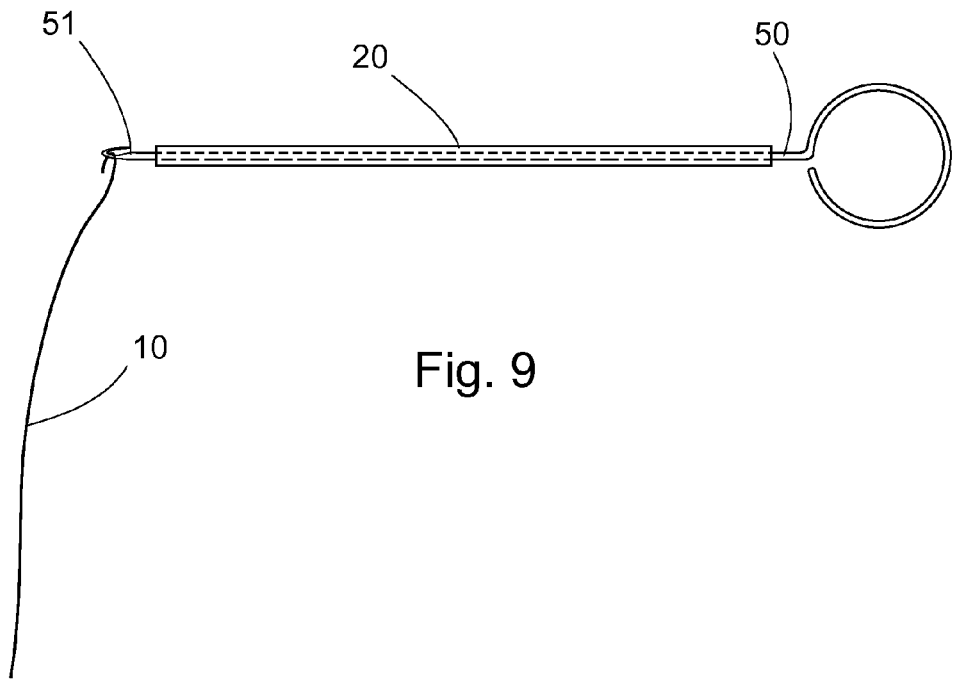
FIG. 9 is a side view schematic illustration of a threading device, a dental tubule, and a dental floss, in accordance with an embodiment of the present invention.

FIG. 9 is a side view schematic illustration of a threading device 50, a dental tubule 20, and a dental floss 10, in accordance with an embodiment of the present invention.

The present illustration shows a stage in one possible production process of the dental floss device 100, according to the present invention.

A hook 51 of a threading device 50, threaded through dental tubule 20 is connected to dental floss 10, which will be later pulled and threaded through the dental tubule 20.

There is a range of options for the measure of compacting force activated by the dental tubule 20 on the dental floss 10, starting from no compacting at all, through a state of compacting resulting from the use of narrow dental tubule 20, a state of compacting as a result of use of a narrow dental tubule 20, to performing a shrink wrap of the dental tubule 20 after completion of threading.

Another good option is to create a state of compacting along only a short segment near the empty segment 22 (shown in FIG. 3*a*). This is advantageous in that only at the beginning on the removal process is there a need for pulling force $F_2$, and most of the length of the dental floss 10 does not come into a contact almost at all with the dental tubule inner surface 20*is* (shown on FIG. 6*c*), so that if it is coated with or immersed in materials, they will not be diminished in the removal process.

The dental tubule 20 can be produced, for example, by coating a metal fiber with a selected compound by an extrusion process that is well known in the electrical wires and fiber optics industries. After completing the coating process the metal fiber can be extracted completely from the coating layer, which can be used as the dental tubule 20.

Figure 10A:
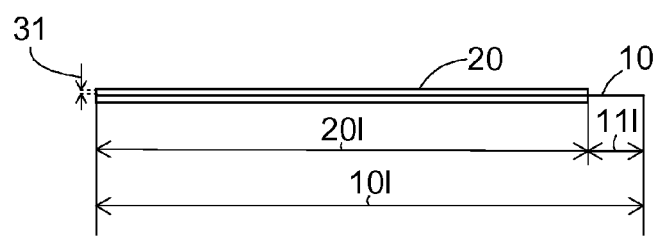
FIG. 10a is a side view schematic illustration of a dental tubule, and a dental floss, at three production process states, in accordance with an embodiment of the present invention.
Figure 10A:
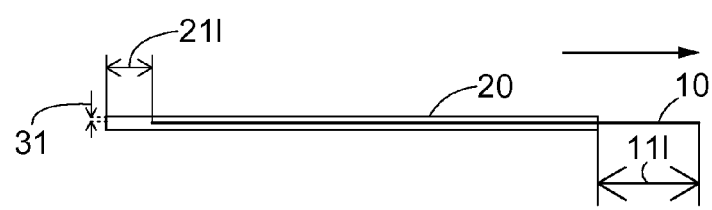
Figure 10A:
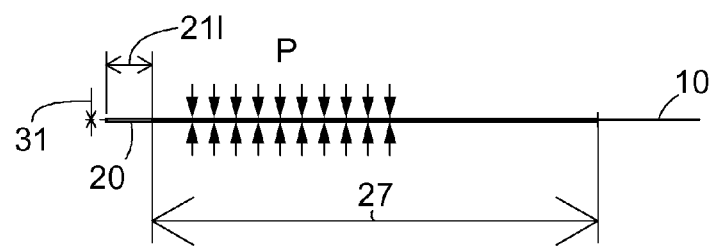

FIG. 10*a* is a side view schematic illustration of a dental tubule 20 and a dental floss 10, in three production process states, in accordance with an embodiment of the present invention.

In the first stage of the three stages, shown in the upper part of the present illustration, a dental floss 10 is disposed within a dental tubule 20, for the entirety of the dental tubule length 20*l* and has an exposed segment 11 on one of its sides.

At this stage, there can be a local gap 31, as was described with regard to FIG. 6, for the entirety of the dental tubule length 20*l*, which is longer than zero, and at any rate, there will be no force between the dental tubule 20 and the dental floss 10 that will effectively disrupt their separation by pulling.

Accordance to another embodiment of the present invention there is not any local gap 31 at this stage.

The second of the three stages is shown in the central part of the illustration, showing the dental floss 10 after having being pulled in the direction of the arrow shown next to it such that the value of the exposed segment length 11*l* grows, and the empty segment length 21*l* is generated. Namely, a shift of the dental floss occurred within the dental tubule 20.

At the end of this stage the dental floss 10 can be cut, equalizing the exposed segment length 11*l* to the empty segment length 21*l*, or in other words, practically equalizing the length of the dental floss 10 to the length of the dental tubule 20.

The last of the three stages is shown at the bottom part of the present illustration, showing a state in which shrinking of the dental tubule 20 was performed, which is mostly manifest in the decrease of the value of dental tubal interior diameter 20*id* (not shown in the present drawing, shown in FIG. 6*a*), generating pressure P of the dental tubule 20 on the dental floss 10 for the entire length of the overlapping zone 27, or part of its length.

A good way of shrinking dental tubule 20 is by making it of a material suitable for shrinking by means of heat at a temperature significantly above room temperature, to a shrunken state that is stable after heating.

Accordance to another embodiment of the present invention the production process does not include this stage.

A preliminary stage to the three stages described above can include cutting to segments of a desired length of a long dental tubule 20, containing a long dental floss 10, exposure of the edges, and performance of the noted stages.

Figure 10B:
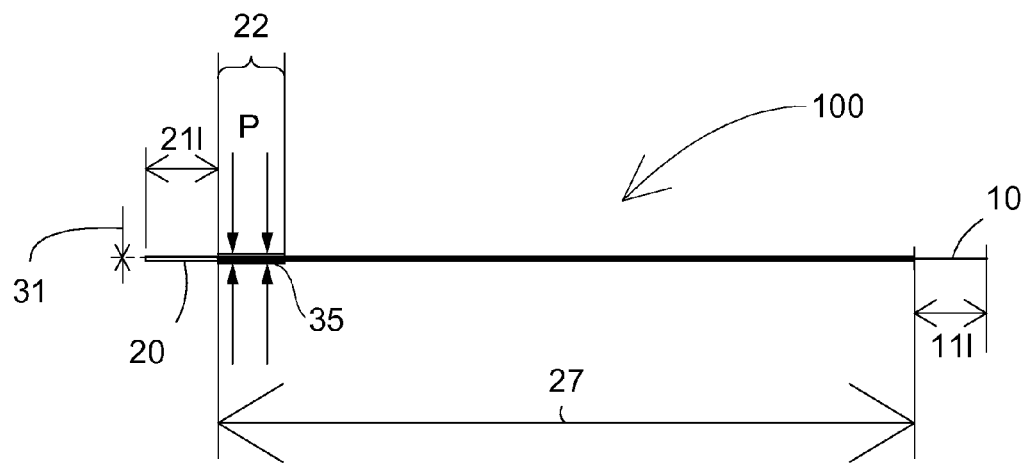
FIG. 10b is a side view schematic illustration of a dental floss device, in accordance with an embodiment of the present invention.

FIG. 10*b* is a side view schematic illustration of a dental floss device 100, in accordance with an embodiment of the present invention.

The exposed segment length 11*l* practically equals the empty segment length 21*l*.

At the segment near the empty segment 22 there is a pressing ring 35 generating pressure P, while over the remaining overlapping zone 27, the pressure P can be negligible. The length of the pressing ring 35 along the dental tubule 20 can be sufficient even in the order of one millimeter. The pressing ring 35 can be made of the same material that the dental tubule 20 is made of, or of another material, rubber, for example.

Figure 11:
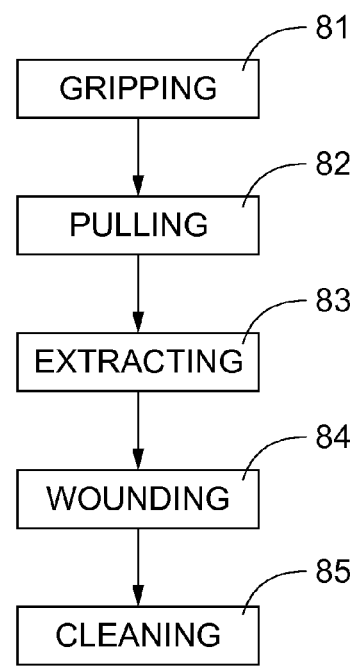
FIG. 11 is a flow chart that schematically illustrates a method for using a dental floss of a dental floss device to floss the teeth of a user, in accordance with an embodiment of the present invention.

FIG. 11 is a flow chart that schematically illustrates a method for using a dental floss of a dental floss device to floss the teeth of a user, in accordance with an embodiment of the present invention.

The method includes the stages of:

gripping with one hand an exposed segment of a dental floss, and gripping with the other hand an empty segment of a dental tubule, wherein the empty segment includes no dental floss (stage 81);

pulling the exposed segment of the dental floss, and pulling with the other hand the empty segment of the dental tubule in an opposite directions (stage 82);

extracting the dental floss fully from the dental tubule (stage 83);

winding edges of the dental floss on the user's own fingers, one from each hand (stage 84); and cleaning between the teeth, with the dental floss that was extracted (stage 85).

Figure 12A:
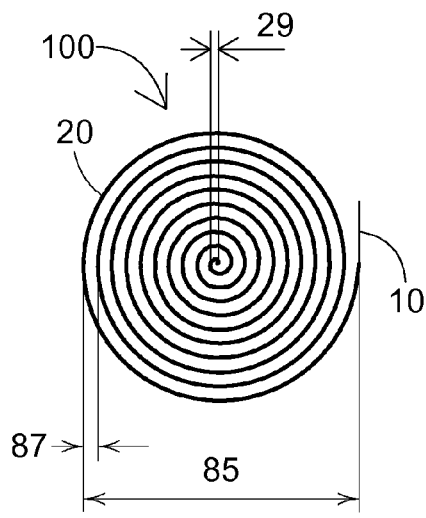
FIG. 12a is a top view schematic illustration of a dental floss device, in accordance with an embodiment of the present invention.

FIG. 12*a* is a top view schematic illustration of a dental floss device 100, in accordance with an embodiment of the present invention.

The dental floss device 100 includes a dental tubule 20, containing a dental floss 10 partly protruding from within the dental tubule 20 and is wound as a planar spiral. This shape is very convenient for storage and carrying of dental floss device 100.

As used herein in the specification and the claims sections 'planar spiral' refers to a planar curve traced by a point which winds about a point from which it continually recedes, and wherein the distance between any two neighboring turns, or in other words, the spiral pitch 87, is substantially constant.

The planar spiral has a spiral outer diameter 85.

The value of the spiral outer diameter 85 can calculated approximately by the equation:

$$D = Pi + (Pi^2 + 4PiL/\pi)^{1/2}$$

wherein:

D=the spiral outer diameter 85;

Pi=the spiral pitch 87; and

L=the dental floss length 10*l*, (shown in FIG. 3*a*).

For example, for a the dental floss length 10*l* of 40 centimeters, having a dental floss cross-sectional area 10A (shown in FIGS. 6*a* and 6*b*) of 0.25 square millimeters, and at a spiral pitch 87 of 1 millimeter, it is possible and sufficient to provide a dental floss device 100 having a planar spiral shape, having a spiral outer diameter 85 of at most 2.5 centimeters. Or in other words, having a spiral outer diameter 85 of at most 0.06 times of the dental floss length 10*l*.

At the most internal segment of the planar spiral, the dental floss device 100 has a bending radius 29 which can be very close to zero if the dental tubule 20 is made of a suitable material and has a suitable dental tubule wall thickness 20*t* and a suitable dental tubule cross-sectional area 20A (both marked on FIG. 6), to enable bending to a similar extent to that of the dental tubule 20.

A practical bending radius 29 of an order of magnitude of 5 millimeters is sufficient. This value, such as other values of technological elements, is chosen value and not a specific discrete value. An example of a chosen value is the given speed limit for a road when it is clear that one mph more or less is not significant, however, for practical purposes, it is useful to establish the speed limit at a specific given number. Another example is the maneuvering limit given to combat pilots in G value. In this case as well, there is no on specific value; however pilots are strictly prohibited from exceeding the known value, so as not to exceed the safety limit. The values for the dimensions and forces noted in the present patent application were chosen in a similar manner.

Figure 12B:
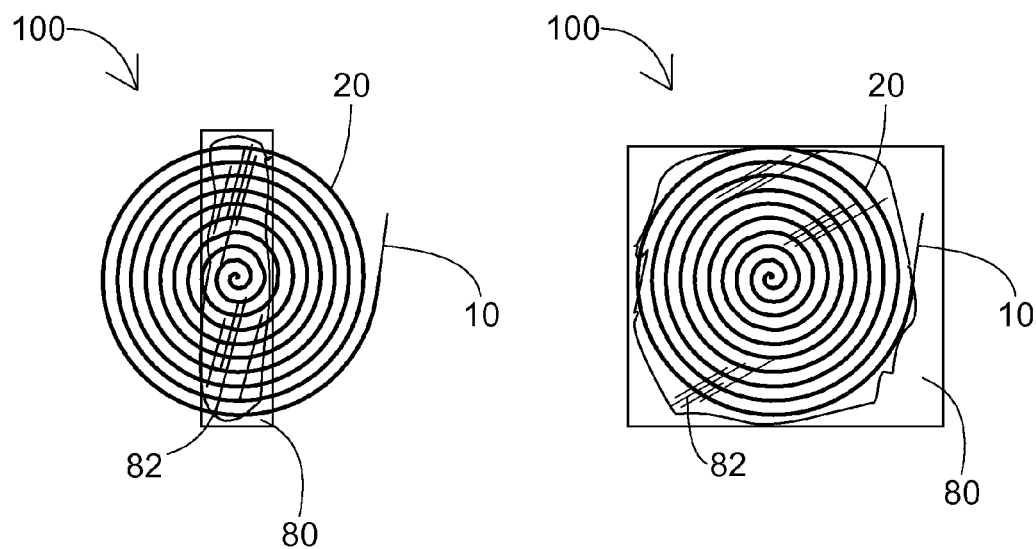
FIG. 12b is a top view schematic illustration of two dental floss devices, in accordance with an embodiment of the present invention.

FIG. 12*b* is a top view schematic illustration of two dental floss devices 100, in accordance with an embodiment of the present invention.

Each dental floss devices 100 includes a dental tubule 20, containing a dental floss 10 partly protruding from within the dental tubule 20. It is wound as a planar spiral and attached to a card 80. The attachment can be by means of an adhesive layer 82.

The adhesive layer 82 can be continuous upon the entire surface area of the card 80 upon which the dental tubule 20 is placed, or on part of it, or even not continuously.

Both parts of the present illustration show cards 80 with different dimensions and shapes and according to the present invention, many different configurations are possible.

This dental floss device 100 is very convenient for storage and portability, and prior to use, the dental tubule 20 and the dental floss 10, namely the dental floss device 100 is removed from the card 80.

While the invention has been described with respect to a limited number of embodiments, it will be appreciated that many variations, modifications and other applications of the invention may be made.

What is claimed is:

1. A dental floss device comprising:
   (a) a collapsible dental tubule having a dental tubule first end and a dental tubule second end; and
   (b) a segment of dental floss having a dental floss first end and a dental floss second end, wherein the segment of dental floss has a length approximately equal to that of said collapsible dental tubule,
   wherein at least a portion of said segment of dental floss is contained within said collapsible dental tubule,
   wherein said dental floss device is capable of having a stored position and a deployed position,
   wherein in said stored position, said collapsible dental tubule together with said segment of dental floss contained at least partially therein are collapsed so as to take up at least 70 percent of a spherical volume encapsulating the collapsed dental floss device, and
   wherein in said deployed position, said collapsible dental tubule is capable of being extended linearly, thereby enabling said dental floss to be fully extracted from said dental tubule.

2. The dental floss device of claim 1, wherein said collapsible dental tubule has a dental tubule inner surface, wherein said dental floss has a dental floss outer surface, wherein said dental floss device has an overlapping zone wherein in said overlapping zone there is full contact between said dental floss outer surface and said dental tubule inner surface, wherein said dental tubule substantially presses on said dental floss along substantially the entirety of said overlapping zone.

3. The dental floss device of claim 1, wherein said dental floss device has a dental floss device length of at most 50 centimeters, wherein said dental floss device is adapted to take a form of a skein, that is suitable to fill most of said spherical volume, by applying a pressing force of at most 3 Newton.

4. The dental floss device of claim 1, wherein said dental floss has an exposed segment which extends longitudinally beyond said second end of said dental tubule.

5. The dental floss device of claim 1, wherein said dental tubule has an empty segment, wherein said empty segment includes no dental floss.

6. The dental floss device of claim 1, wherein a force required for bending said dental floss device to a particular bending radius is substantially the same as a force required for bending said dental floss to said particular bending radius.

7. The dental floss device of claim 1,
   wherein said dental floss has a dental floss cross-sectional area $A_F$,
   wherein said dental tubule has a dental tubule interior diameter d, and a dental tubule wall thickness t, such that the dental tubule annular cross-sectional area $A_T$ is approximately $A_T = \pi \cdot d \cdot t$, and
   wherein $A_T = 3 \cdot A_F$.

8. The dental floss device of claim 7, wherein $A_T = 2 \cdot A_F$.

9. The dental floss device of claim 8, wherein $A_T = A_F$.

10. The dental floss device of claim 1, wherein said dental floss has a dental floss cross-sectional area AF, such that said dental floss has an equivalent radius $r = \sqrt{A_F/\pi}$, wherein said dental tubule had a dental tubule wall thickness t, and wherein $t = 0.5 \cdot r$.

11. A dental floss device comprising:
    (a) a collapsible dental tubule having a dental tubule first end, a dental tubule second end, a dental tubule length, and a dental tubule inner surface; and
    (b) a segment of dental floss having a dental floss first end, a dental floss second end, a dental floss length substantially equal to said length of said dental tubule, and a dental floss outer surface, wherein at least most of said dental floss is contained within said dental tubule, wherein said dental floss device is adapted to be provided with a shape of a planar spiral having a spiral outer diameter, wherein said spiral outer diameter equals at most 0.06 times said dental floss length, and wherein said dental floss device is adapted to enable extracting of said dental floss fully from said dental tubule.

12. The dental floss device of claim 11, wherein said dental floss device has an overlapping zone wherein in said overlapping zone there is full contact between said dental floss outer surface and said dental tubule inner surface, wherein said dental tubule substantially presses on said dental floss along substantially the entirety of said overlapping zone.

13. The dental floss device of claim 11, wherein said dental floss has an exposed segment which extends longitudinally beyond said second end of said dental tubule.

14. The dental floss device of claim 11, wherein said dental tubule has an empty segment, wherein said empty segment includes no dental floss.

15. A dental floss device comprising:
    (a) a dental tubule having a dental tubule first end, a dental tubule second end, a dental tubule circumference, a dental tubule wall thickness, a dental tubule annular cross-sectional area value, a dental tubule length, and a dental tubule inner surface; and
    (b) a dental floss having a dental floss first end, a dental floss second end, a dental floss length, a dental floss cross-sectional area value, and a dental floss outer surface, wherein at least most of said dental floss is contained within said dental tubule, wherein said dental tubule annular cross-sectional area value is equal at most to a pre-determined n times the dental floss cross-sectional area value, wherein said n-value is selected from a group consisting of one, two and three, and wherein said dental floss device is adapted to enable extracting of said dental floss fully from said dental tubule.

16. The dental floss device of claim 15 wherein said dental floss device has an overlapping zone, wherein in said overlapping zone there is full contact between said dental floss outer surface and said dental tubule inner surface, wherein said dental tubule substantially presses on said dental floss along substantially the entirety of said overlapping zone, and said dental floss length approximately equals said length of said dental tubule.

17. The dental floss device of claim 15, wherein said dental tubule has bending characteristics such that said dental tubule does not create any substantial bending restriction on a segment of said dental floss contained within said dental tubule in said overlapping zone.

18. The dental floss device of claim 15, wherein said dental floss has an exposed segment which extends longitudinally beyond said second end of said dental tubule, wherein said dental floss device has a dental floss device volume, wherein said dental floss device is adapted to be inserted into a ball having a ball internal volume, and wherein said ball internal volume equals at most 1.45 times said dental floss device volume.

19. The dental floss device of claim 15, wherein said dental tubule has an empty segment, wherein said empty segment includes no dental floss.

20. The dental floss device of claim 17, wherein said dental floss has an exposed segment which extends longitudinally beyond said second end of said dental tubule.

21. The dental floss device of claim 17, wherein said dental tubule has an empty segment, wherein said empty segment includes no dental floss.

22. The dental floss device of claim 15, wherein said dental tubule has a dental tubule interior volume, wherein said dental floss has a dental floss volume, and wherein said dental tubule interior volume approximately equals said dental floss volume.

23. The dental floss device of claim 15, wherein said dental tubule has an empty segment having an empty segment length, wherein said dental floss has an exposed segment having an exposed segment length, and wherein said empty segment length approximately equals said exposed segment length.

24. The dental floss device of claim 15, wherein said dental tubule has a dental tubule weight, wherein there is a dental tubule segment near the dental floss second end, wherein said segment is at most ten percent of said overlapping zone, wherein said dental tubule segment near the dental floss second end produce pressure acting on said dental floss at said segment near the dental floss second end, wherein said pressure is stronger than any other pressure applied by said dental tubule on said dental floss at any segment other than said segment near the dental floss second end, and wherein a pulling force needed for extraction said dental floss from said dental tubule equals at most said dental tubule weight.

25. The dental floss device of claim 24 wherein said dental floss device further comprises:
   (c) a pressing ring mounted on said dental tubule at said segment near the dental floss second end.

* * * * *